United States Patent [19]

Yasuda et al.

[11] Patent Number: 5,436,145

[45] Date of Patent: Jul. 25, 1995

[54] PROCESS FOR PREPARING 6-HYDROXY NITROGEN-CONTAINING 6-MEMBERED RING COMPOUNDS

[75] Inventors: Mari Yasuda, Yokohama; Haruyuki Ohkishi, Machida; Katsutoshi Sato, Machida; Yuuki Morimoto, Machida; Toru Nagasawa, Nagoya, all of Japan

[73] Assignee: Mitsubishi Kasei Corporation, Tokyo, Japan

[21] Appl. No.: 246,570

[22] Filed: May 20, 1994

Related U.S. Application Data

[63] Continuation of Ser. No. 22,135, Feb. 25, 1993, abandoned.

[30] Foreign Application Priority Data

Feb. 26, 1992 [JP] Japan ................................. 4-039562
Mar. 31, 1992 [JP] Japan ................................. 4-077461

[51] Int. Cl.$^6$ ............................................. C12P 17/12
[52] U.S. Cl. ............................... 435/122; 435/822; 435/824; 435/840; 435/843; 435/847; 435/850; 435/859; 435/874; 435/876; 435/877; 435/880; 435/881
[58] Field of Search .......................................... 435/122

[56] References Cited

U.S. PATENT DOCUMENTS

| | | | |
|---|---|---|---|
| 4,738,924 | 4/1988 | Kulla ..................... | 435/121 |
| 5,082,777 | 1/1992 | Lehky ..................... | 435/122 |
| 5,151,351 | 9/1992 | Hoeks ..................... | 435/122 |
| 5,173,412 | 12/1992 | Kiener et al. ............. | 435/122 |
| 5,182,197 | 1/1993 | Kiener et al. ............. | 435/122 |

FOREIGN PATENT DOCUMENTS

| | | | |
|---|---|---|---|
| 2052063 | 3/1992 | Canada ..................... | 435/122 |
| 0434035 | 6/1991 | European Pat. Off. . | |
| 0466042 | 1/1992 | European Pat. Off. . | |
| 0466115 | 1/1992 | European Pat. Off. . | |

(List continued on next page.)

OTHER PUBLICATIONS

Jones, J. B. "Enzymes in Organic Synthesis", vol. 42, No. 13, pp. 3351-3403, 1986.

Yamamoto et al., Chemical Abstracts, vol. 107 (1989), p. 15 Abstract No. 228395w.

Foks et al., Chemical Abstracts, vol. 66 (1967), p. 8898 Abstract No. 94996s.

Ikeda Shokuken, Database WPI Section Ch. Week 9250—Derwent Publications London GB AN9-2-409786 JP-A-4 304 893.

(List continued on next page.)

Primary Examiner—Marian C. Knode
Assistant Examiner—S. Saucier
Attorney, Agent, or Firm—Wenderoth, Lind & Ponack

[57] ABSTRACT

6-Hydroxy nitrogen-containing 6-membered ring compounds of the following general formula (II):

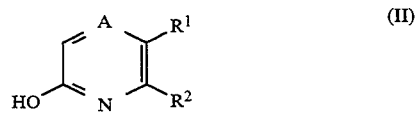

(II)

wherein $R^1$ represents carboxy group, carbamoyl group, cyano group, formyl group, $C_1$–$C_5$ hydroxyalkyl group, $C_2$–$C_6$ alkoxycarbonyl group, carboxyvinyl group, carboxymethyl group or oxime group, $R^2$ represents hydrogen atom or carboxy group, and A represents carbon atom or nitrogen atom, can be prepared by reacting a nitrogen-containing 6-membered ring compounds of the following general formula (I):

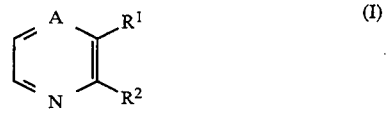

(I)

wherein $R^1$, $R^2$ and A are as defined in the general formula (II) above, with a microorganism or physicochemically treated microorganism in an aqueous medium. Efficiency of the above reaction can be raised by conducting the reaction in the presence of phenazine methosulfate.

2 Claims, No Drawings

FOREIGN PATENT DOCUMENTS

| | | |
|---|---|---|
| 0477829 | 4/1992 | European Pat. Off. |
| 0498316 | 8/1992 | European Pat. Off. |
| 0504818 | 9/1992 | European Pat. Off. |
| 0504819 | 9/1992 | European Pat. Off. |
| 0519512 | 12/1992 | European Pat. Off. |
| 0529653 | 3/1993 | European Pat. Off. |
| 0556465 | 8/1993 | European Pat. Off. |

OTHER PUBLICATIONS

Mitsubishi Chem., Chemical Abstracts, vol. 120 (1994) p. 960 Abstract No. 161783u.

Jerald C. Ensign and Sydney Rittenberg, *The Pathway of Nicotinic Acid Oxidation by Bacillus Species,* 239(7) J. Biol. Chem. 2285 (Jul. 1964).

Rona Hirschberg and J. C. Ensign, *Oxidation of Nicotinic Acid by a Bacillus Species: Purification and Properties of Nicotinic Acid and 6-Hydroxynicotnic Acid Hydroxylases,* 108(2) J. Bacteriology 751 (1971).

Rona Hirschberg and J. C. Ensign, *Oxidation of Nicotinic Acid by a Bacillus Species: Source of Oxygen Atoms for the Hydroxylation of Nicotinic Acid and 6-Hydroxynicotinic Acid,* 108(2) J. Bacteriology 757 (1971).

Hans G. Kulla, *Enzymatic Hydroxylations in Industrial Application,* 45(3) Chimia 81 (1991).

PROCESS FOR PREPARING 6-HYDROXY NITROGEN-CONTAINING 6-MEMBERED RING COMPOUNDS

This application is a continuation of now abandoned application, Ser. No. 08/022,135, filed Feb. 25, 1993, now abandoned.

The present invention relates to a process for preparing 6-hydroxy nitrogen-containing 6-membered ring compounds. More particularly, this invention relates to a process for preparing 6-hydroxypyridine derivatives and 6-hydroxypyrazine derivatives, which are useful as intermediates for preparing medicines, agricultural chemicals, dyestuffs or the like, taking advantage of microbial reaction.

Various nitrogen-containing 6-membered ring compounds such as dihydropyridines, nicotinic acids and the like, can be important synthetic intermediates for preparing medicines, agricultural chemicals, dyestuffs or the like. For example, new types of insecticides which act on nicotinic acid receptors have recently being studied, and Imidacloprid (Nippon Tokushu Noyaku Co.) represented by the following formula is one of the new insecticides.

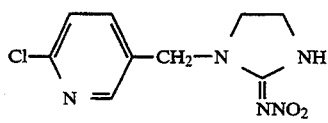

As the intermediate for the preparation of Imidacloprid, 3-chloromethyl-6-chloropyridine is very important.

Various synthetic routes for preparing the pyridines having substituents at 3- and 6-positions have been intensively studied thus far. However, there is no method for selectively introducing a substituent at the 6-position of a 3-substituted pyridine by the method of organic chemistry. On the other hand, a process for introducing a hydroxy group at the 6-position of nicotinic acid using a microorganism belonging to genus Pseudomonas, genus Bacillus or genus Achromobacter, which is capable of decomposing nicotinic acid, has been described in Japanese Patent Publication (KOKAI) Nos. 60-196193 and 60-196194. However, it is necessary to express the activity more effectively for putting the above process into practical use. There is no report on other 3-substituted nitrogen-containing 6-membered ring compounds.

The present invention is directed to a process for preparing 6-hydroxy nitrogen-containing 6-membered ring compounds of the following general formula (II):

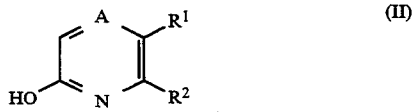

wherein $R^1$ represents carboxy group, carbamoyl group, cyano group, formyl group, $C_1-C_5$ hydroxyalkyl group, $C_2-C_6$ alkoxycarbonyl group, carboxyvinyl group, carboxymethyl group or oxime group, $R^2$ represents hydrogen atom or carboxy group, A represents carbon atom or nitrogen atom, with the proviso that when $R^2$ is hydrogen atom and A is carbon atom, $R^1$ is not a carboxy group, which process comprises reacting nitrogen-containing 6-membered ring compound of the following general formula (I):

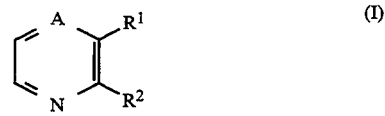

wherein $R^1$, $R^2$ and A are as defined in the general formula (II), with a microorganism or physico-chemically treated microorganism in an aqueous medium.

The present invention will be explained in more detail below.

The 6-hydroxy nitrogen-containing 6-membered ring compounds produced by the present invention are represented by the general formula (II) above. The $C_1-C_5$ hydroxyalkyl group as defined by $R^1$ illustratively includes hydroxymethyl group, 1-hydroxyethyl group, 2-hydroxyethyl group, 3hydroxypropyl group, 4-hydroxybutyl group and the like, and the $C_2-C_6$ alkoxycarbonyl group includes methoxycarbonyl group, ethoxycarbonyl group, n-propoxycarbonyl group, i-propoxycarbonyl group, n-butoxycarbonyl group and the like.

The starting nitrogen-containing 6-membered ring compounds of the general formula (I) include nicotinamide, 3-cyanopyridine, quinolinic acid, nicotinaldehyde, pirazinamide and the like. The corresponding 6-hydroxy nitrogen-containing 6-membered ring compounds can be prepared according to the process of the present invention.

Preferable microorganisms used in the present invention illustratively include a microorganism selected from the microorganisms belonging to Genus Agrobacterium, Genus Arthrobacter, Genus Bordetella, Genus Brevibacterium, Genus Pseudomonas, Genus Achromobacter, Genus Comamonas, Genus Erwinia, Genus Bacterium, Genus Corynebacterium, Genus Serratia, Genus Sarcina, Genus Xanthobacter, Genus Alcaligenes, Genus Flavobacterium Genus and Genus Micrococcus. These microorganisms which have been physico-chemically treated can also be employed. Microorganisms usable in the process of the present invention should not be restricted to the above-listed organisms as far as they have an ability to selectively introduce a hydroxyl group at the 6-position of the nitrogen-containing 6-membered ring compounds of the general formula (I).

The microorganisms belonging to Genus Agrobacterium illustratively include *Agrobacterium radiobacter, Agrobacterium tumefaciens, Agrobacterium viscosum* and the like. More specifically, there are exemplified *Agrobacterium radiobacter* NRRL B-11291 (Agricultural Research Service Culture Collection), *Agrobacterium tumefaciens* IAM 13129 (Research Institute of Applied Microbiology, Tokyo University), *Agrobacterium viscosum* IFO 13652 (Institute for Fermentation, Osaka), etc.

The microorganisms belonging to Genus Arthrobacter illustratively include *Arthrobacter globiformis, Arthrobacter fragilis* and the like. More specifically, there are exemplified *Arthrobacter globiformis* IFO 12137 (Institute for Fermentation, Osaka), *Arthrobacter fragilis* FERM P-4350 (Fermentation Research Institute, Agency of Industrial Science and Technology), etc.

The microorganisms belonging to Genus Bordetella illustratively include *Bordetella bronchiseptica* and the like. More specifically, there are exemplified *Bordetella bronchiseptica* ATCC 4617 (American Type Culture Collection) etc.

The microorganisms belonging to Genus Brevibacterium illustratively include *Brevibacterium butanicum*, *Brevibacterium ketoglutamicum* and the like. More specifically, there are exemplified *Brevibacterium butanicum* ATCC 21196 (American Type Culture Collection), *Brevibacterium ketoglutamicum* ATCC 15587 (American Type Culture Collection), etc.

The microorganisms belonging to Genus Pseudomonas illustratively include *Pseudomonas dacunhae*, *Pseudomonas maltophila*, *Pseudomonas chlororaphis*, *Pseudomonas hydantoinophilum*, *Pseudomonas putida*, *Pseudomonas fluorescens* and the like. More specifically, there are exemplified *Pseudomonas dacunhae* AtCC 13261 (American Type Culture Collection), *Pseudomonas maltophila* ATCC 13637 (American Type Culture Collection), *Pseudomonas chlororaphis* IFO 3904 (Institute for Fermentation, Osaka), *Pseudomonas hydantoinophium* FERM P-4347 (Fermentation Research Institute, Agency of Industrial Science and Technology), *Pseudomonas putida* ATCC 21244 (American Type Culture Collection), *Pseudomonas fluorescens* IFO 3903 (Institute for Fermentation, Osaka), etc.

The microorganisms belonging to Genus Achromobacter illustratively include *Achromobacter xerosis* and the like. More specifically, there are exemplified *Achromobacter xerosis* IFO 12668 (Institute for Fermentation, Osaka), etc.

The microorganisms belonging to Genus Comamonas illustratively include *Comamonas acidovorans*, *Comamonas testosteroni* and the like. More specifically, there are exemplified *Comamonas acidovorans* NCIMB 9289 (National Collection of Industrial And Marine Bacteria Ltd.), *Comamonas testosteroni* ATCC 11996 (American Type Culture Collection), etc.

The microorganisms belonging to Genus Erwinia illustratively include *Erwinia herbicola* and the like. More specifically, there are exemplified *Erwinia herbicola* ATCC 21434 (American Type Culture Collection), etc.

The microorganisms belonging to Genus Bacterium illustratively include *Bacterium cyclo-oxydans* and the like. More specifically, there are exemplified *Bacterium cyclo-oxydans* ATCC 12673 (American Type Culture Collection), etc.

The microorganisms belonging to Genus Corynebacterium illustratively include *Corynebacterium xerosis* and the like. More specifically, there are exemplified *Corynebacterium xerosis* NCTC 9755 (National Collection of Type Cultures), etc.

The microorganisms belonging to Genus Serratia illustratively include *Serratia liquefaciens*, *Serratia marcescens* and the like. More specifically, there are exemplified *Serratia liquefaciens* IFO 12979 (Institute for Fermentation, Osaka), *Serratia marcenscens* IFO 3054 (Institute for Fermentation, Osaka), *Serratia marcenscens* IFO 12648 (Institute for Fermentation, Osaka), etc.

The microorganisms belonging to Genus Sarcina illustratively include *Sarcina lutea* and the like. More specifically, there are exemplified *Sarcina lutea* ATCC 9341 (American Type Culture Collection), etc.

The microorganisms belonging to Genus Xanthobacter illustratively include *Xanthobacter flavus* and the like. More specifically, there are exemplified *Xanthobacter flavus* NCIMB 10071 (National Collections of Industrial And Marine Bacteria Ltd.), etc.

The microorganisms belonging to Genus Alcaligenes illustratively include *Alcaligenes eutrophus*, *Alcaligenes aquamarinus*, *Alcaligenes faecalis* and the like. More specifically, there are exemplified *Alcaligenes eutrophus* ATCC 17699 (American Type Culture Collection), *Alcaligenes aquamarinus* FERM P-4229 (Fermentation Research Institute, Agency of Industrial Science and Technology), *Alcaligenes faecalis* IFO 13111 (Institute for Fermentation, Osaka), etc.

The microorganisms belonging to Genus Flavobacterium illustratively include *Flavobacterium suaveolens*, *Flavobacterium aminogenes*, *Flavobacterium arborescens*, *Flavobacterium dehydrogenans*, *Flavobacterium heparinum* and the like. More specifically, there are exemplified *Flavobacterium suaveolens* IFO 3752 (Institute for Fermentation, Osaka), *Flavobacterium aminogenes* FERM P-3134 (Fermentation Research Institute, Agency of Industrial Science and Technology), *Flavobacterium arborescens* IFO 3750 (Institute for Fermentation, Osaka), *Flavobacterium dehydrogenans* ATCC 13930 (American Type Culture Collection), *Flavobacterium heparinum* IFO 12017 (Institute for Fermentation, Osaka), etc.

The microorganisms belonging to Genus Micrococcus illustratively include *Micrococcus varians*, *Micrococcus morrhuae* and the like. More specifically, there are exemplified *Micrococcus varians* IAM 1314 (Institute of Applied Microbiology, The University of Tokyo), *Micrococcus morrhuae* IAM 1711 (Institute of Applied Microbiology, The University of Tokyo), etc.

Nutrients necessary for cultivation of these microorganisms have no limitation, and conventional nutrients used for microorganisms can be used. For example, carbon sources include sugars such as glucose, sucrose, fructose, glycerol, sorbitol, molasses, starch hydrolysate or the like, and organic acids such as acetic acid, fumaric acid or the like. Nitrogen sources include nitrates, ammonium salts, corn steep liquor, yeast extract, meat extract, yeast powder, soy bean hydrolysate, cotton seed dust, polypeptone, Benton and the like. Minerals include potassium phosphate, calcium phosphate, sodium phosphate, magnesium sulfate, manganese sulfate, sodium chloride and the like. Minerals such as sources of iron ion, cobalt ion, copper ion or the like may be favorably added to the culture for inducing the production of enzymes.

Cultivation may be favorably effected under aerobic conditions at temperature from 20° to 40° C., preferably 30° to 35° C., at pH 4.0 to 9.0, preferably pH 5.0 to 7.0 over a period of 20 to 24 hours, until population of microorganisms increases up to about $OD_{660}$ to $OD_{660}$ 40.

The "physico-chemically treated microorganism" in the present invention means the microorganism extracts, pulverized microorganism, and their purified product obtained by known methods such as separation by ammonium sulfate, ion exchange chromatography, gel filtration or the like. In the process of the present invention, the nitrogen-containing 6-membered ring compound (I) may be reacted with a microorganism itself (living cell or dried cell) or physico-chemically treated microorganism.

The microorganism obtained by the cultivation or physico-chemically treated microorganism can be fixed on a gel, such as polyacrylamide gel, photo-crosslinking resin, carrageenan or the like, and then allowed to react with the nitrogen-containing 6-membered ring compound (I).

When Compound (I) is allowed to react with a microorganism per se, Compound (I) may be added to the microorganism which has been sufficiently grown. Appropriate concentration of the nitrogen-containing 6-membered ring compound (I) is between 0.1% by weight and the saturated concentration, preferably 1.0 to 5.0% by weight. The reaction is carried out at temperature from 20° to 50° C., preferably 30° to 40° C., at pH 4.0 to 9.0, preferably 5.0 to 7.0, over a period of 2 to 24 hours, ordinarily 20 to 24 hours, under aerobic conditions and with stirring.

When Compound (I) is allowed to react with physico-chemically treated microorganism, the compound is added to an aqueous solution, such as 0.01 to 1M phosphate buffer (pH 6–9) containing about 2 to 15 mg (protein weight) of microorganism extract or pulverized microorganism.

When the microorganism per se or treated microorganism is fixed, the nitrogen-containing 6-membered compound (I) is reacted with the fixed microorganism under the above-mentioned conditions in a reactor equipped with a stirrer. Alternatively, a liquid containing the nitrogen-containing 6-membered ring compound is passed through a column filled with the fixed microorganism.

Efficiency of the hydroxylation can be raised in the process of the present invention by effecting the reaction in the presence of phenazine methosulfate. In this case, phenazine methosulfate (N-methylphenazonium methosulfate or 5-methylphenaziniummethyl sulfate) is needed to exist in the reaction mixture. More specifically, phenazine methosulfate may be added together with Compound (I) at a time for the reaction with the microorganism per se or treated microorganism. Appropriate concentration of phenazine methosulfate in the reaction mixture is 1 to 100 mM, preferably 5 ,to 100 mM.

The aqueous medium used in the present invention may be water or a buffer such as acetate buffer, phosphate buffer or the like. An excessive amount of said aqueous medium for Compound (I) as a substrate is preferred.

The 6-hydroxy nitrogen-containing 6-membered ring compounds thus obtained can be extracted in a conventional manner from the reaction mixture with a solvent such as methanol, water or the like, and purified by column chromatography filled with ODS resin or the like.

The 6-hydroxy nitrogen-containing 6-membered ring compounds (II), such as 3-cyano-6-hydroxypyridine, obtained in the present invention are useful as intermediates for the preparation of medicines, agricultural chemicals, dyestuffs or the like. For example, 3-cyano-6-hydroxypyridine can be easily converted by a conventional method into 3-chloromethyl-6-hydroxypyridine, an intermediate for agricultural chemicals.

The following detailed Examples are presented by way of illustration of certain specific embodiments of the invention. The Examples are representative only and should not be construed as limiting in any respect.

EXAMPLE 1

To an Erlenmeyer flask equipped with navels was filled a nutrient solution containing 1 g of yeast extract, 1 g of glucose, 0.3 g of $K_2HPO_4$, 0.1 g of $KH_2PO_4$, 1 mg of $FeSO_4$, 50 mg of $MgSO_4$, 1 mg of $MnSO_4$ and 100 ml of water, and the resultant mixture was sterilized at 120° C. for 20 minutes. After cooling to 30° C., the mixture was added with separately sterilized 1 mg of $CuSO_4$ and 0.2 g of 3-cyanopyridine as an inducer. One of the microorganisms listed in Table 1 which was incubated on nutrient agar medium for 24 hours was inoculated into the above mixture with a platinum loop, and the mixture was incubated at 30° C. for 24 hours using a rotary shaker of 160 rpm. After 24 hours, the broth was recovered and centrifuged. The cells separated were suspended in and washed with 0.02 mol of an acetate buffer (pH 5.5) and centrifuged to give a resting cell. To a 100 ml reactor was added 20 ml of 1.0% 3-cyanopyridine (pH 5.5), and the mixture was heated at 30° C., and mixed with the resting cell obtained above. The resultant mixture was stirred sufficiently for 24 hours to give 3-cyano-6-hydroxypyridine. The product was identified by means of HPLC, IR and $^1H$-NMR. Table 1 shows the results.

TABLE 1

| Microorganisms used | Yield (mg) |
| --- | --- |
| Achromobacter xerosis (IFO 12668) | 2.0 |
| Agrobacterium radiobacter (NRRL B-11291) | 1.0 |
| Alcaligenes eutrophus (ATCC 17699) | 3.0 |
| Alcaligenes aquamarinus (FERM P-4229) | 2.0 |
| Alcaligenes faecalis (IFO 13111) | 2.0 |
| Arthrobacter globiformis (IFO 12137) | 3.0 |
| Arthrobacter fragilis (FERM P-4350) | 2.0 |
| Bacterium cyclo-oxydans (ATCC 12673) | 13.0 |
| Bordetella bronchiseptica (ATCC 4617) | 10.0 |
| Brevibacterium butanicum (ATCC 21196) | 12.0 |
| Brevibacterium ketoglutamicum (ATCC 15587) | 2.0 |
| Corynebacterium xerosis (NCTC 9755) | 19.0 |
| Erwinia herbicola (ATCC 21434) | 2.0 |
| Flavobacterium suaveolens (IFO 3752) | 1.0 |
| Micrococcus varians (IAM 1314) | 1.0 |
| Micrococcus morrhuae (IAM 1711) | 1.0 |
| Comamonas acidovorans (NCIMB 9289) | 72.0 |
| Comamonas testosteroni (ATCC 11996) | 24.0 |
| Pseudomonas dacunhae (ATCC 13261) | 12.0 |
| Pseudomonas maltophila (ATCC 13637) | 19.0 |
| Pseudomonas chlororaphis (IFO 3904) | 1.0 |
| Pseudomonas hydantoinophilum (FERMP-4347) | 5.0 |
| Pseudomonas putida (ATCC 21244) | 1.0 |
| Sarcina lutea (ATCC 9341) | 3.0 |
| Serratia liquefaciens (IFO 12979) | 1.0 |
| Serratia marcescens (IFO 3054) | 1.0 |
| Serratia marcescens (IFO 12648) | 2.0 |
| Xanthobacter flavus (NCIMB 10071) | 1.0 |

$^1H$-NMR (DMSO-$d_6$) δ: 6.42 (1H, d, $J_{4,5}=9.9$ Hz, H-5), 7.67 (1H, dd, $J_{4,5}=9.9$ Hz, $J_{2,4}=2.4$ Hz, H-4), 8.26 (1H, d, $J_{2,4}=2.4$ Hz, H-2), 12.40 (1H, bs, OH)

EXAMPLE 2

A Sakaguchi flask was filled with a nutrient solution (pH 7.0) containing 1 g of meat extract, 1 g of malic acid, 0.1 g of $K_2HPO_4$, 1 g of nicotinic acid, 500 mg of $MgSO_4·7H_2O$ and 100 ml of water, and the content was sterilized at 120° C. for 20 minutes. After cooling to 30° C., 2 ml of a sterilized metallic solution (shown in Table 2) was added. After incubation for 24 hours on nutrient agar medium, one platinum loop of each of Serratia marcescens (IFO 12648) and Pseudomonas fluorescens (IFO 3903) was inoculated and incubated at 30° C. for 36 hours in a reciprocal shaker. After recovering the cultivated product, the cells were centrifuged. The separated cells were suspended in and washed with 0.1 mol of a phosphate buffer (pH 7.0) and centrifuged to give the cells. The resultant cells were pulverized by supersonic wave and subjected to ultracentrifugation. The resultant precipitate was mixed with and suspended in 0.3% Triton X and 0.1% cetylpyridinium chloride on ice for 1 hour and again subjected to ultracentrifugation. The supernatant was used as a crude enzyme solution. The precipitate was again subjected to the same procedure, and the supernatant was added to the crude enzyme solution. The crude enzyme solution was purified by column chromatography on DEAE Sephacel, Phenyl Sepharose, Butyl Toyopearl or the like. The reaction was initiated by mixing 100 μl of the enzyme solution with 1.5 mM DCIP (2,6-Dichloroindophenol), 2.0 ml of 0.1 M phosphate buffer (pH 7.0), 100 μl of 3.0 mM PMS (phenazine methosulfate), and 500 μl of 2 mM-5 mM substrate solution as shown in Table 2. After finishing the reaction at 30° C. for 1 minute, an activity was assayed by measuring the change of absorbance at 600 nm. Table 3 shows the test results.

TABLE 2

Composition of the Metallic Solution

| Metal | /L of DW |
|---|---|
| $CaCl_2.2H_2O$ | 400 mg |
| $H_3BO_3$ | 500 mg |
| $CuSO_4.5H_2O$ | 40 mg |
| KI | 100 mg |
| $FeSO_4.7H_2O$ | 200 mg |
| $MnSO_4.7H_2O$ | 400 mg |
| $ZnSO_4.7H_2O$ | 400 mg |
| $H_2MoO_4.2H_2O$ | 200 mg |
| HCl | 20 ml |

TABLE 3

| Substrate | S. marcescence IFO 12648 μM | P. fluorescens IFO 3903 μM |
|---|---|---|
| Nicotineamide | 213 | 701 |
| Pyrazine 2,3-dicarboxylic acid | 19 | 3 |
| Nicotinaldehyde | 463 | 825 |
| Pyridyl carbinol | 72 | 857 |
| Pyridyl propanol | N.D | 7 |
| Ethyl nicotinate | 461 | 539 |
| Quinolinic acid | 39 | 15 |
| Trans-3-(3-pyridyl) acrylic acid | 206 | 0.3 |
| 3-Pyridyl acetic acid | 91 | 47 |
| Pyrazine amido | 17 | 14 |
| 3-Pyridinealdoxime | 293 | 333 |
| 3-Cyanopyridine | 33 | 11 |

N.D.: not determined

It was found from the results of Examples 1 and 2 that the hydroxy group can be selectively introduced at the 6-position of the nitrogen-containing 6-membered ring compound by the action of the microorganisms used.

What we claim is:

1. A process for preparing 3-cyano-6-hydroxypyridine of the formula:

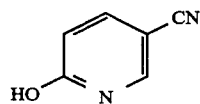

which process comprises reacting 3-cyanopyridine of the formula:

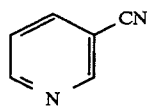

with a microorganism selected from the group consisting of
Achromobacter xerosis,
Agrobacterium radiobacter,
Alcaligenes eutrophus,
Alcaligenes aquamarinus,
Alcaligenes faecalis,
Arthrobacter globiformis,
Arthrobacter fragilis,
Bacterium cyclo-oxydans,
Bordetella bronchiseptica,
Brevibacterium butanicum,
Brevibacterium ketoglutamicure,
Corynebacterium xerosis,
Erwinia herbicola,
Flavobacterium suaveolens,
Micrococcus varians,
Micrococcus morrhuae,
Comamonas acidovorans,
Comamonas testosteroni,
Pseudomonas fluorescens,
Pseudomonas dacunhae,
Pseudomonas maltophila,
Pseudomonas chlororaphis,
Pseudomonas hydantoinophilum,
Pseudomonas putida,
Sarcina lutea,
Serratia liquefaciens,
Serratia marcescens, and
Xanthobacter flavus
or with an extract derived from any one of the said microorganisms in an aqueous medium, and recovering 3-cyano-6-hydroxypyridine from the medium.

2. A process according to claim 1 wherein the microorganism is selected from the group consisting of
Achromobacter xerosis (IFO 12668),
Agrobacterium radiobacter (NRRL B-11291),
Alcaligenes eutrophus (ATCC 17699),
Alcaligenes aquamarinus (FERM P-4229),
Alcaligenes faecalis (IFO 13111),
Arthrobacter globiformis (IFO 12137),
Arthrobacter fragilis (FERM P-4350),
Bacterium cyclo-oxydans (ATCC 12673),
Bordetella bronchiseptica (ATCC 4617),
Brevibacterium butanicum (ATCC 21196),
Brevibacterium ketoglutamicum (ATCC 15587),
Corynebacterium xerosis (NCTC 9755),
Erwinia herbicola (ATCC 21434 ),
Flavobacterium suaveolens (IFO 3752),
Micrococcus varians (IAM 1314),
Micrococcus morrhuae (IAM 1711),
Comamonas acidovorans (NCIMB 9289),
Comamonas testosteroni (ATCC 11996),
Pseudomonas fluorescens ( IFO 3903),
Pseudomonas dacunhae (ATCC 13261) ,
Pseudomonas maltophila (ATCC 13637),
Pseudomonas chlororaphis (IFO 3904),
Pseudomonas hydantoinophilum (FERM P-4347),
Pseudomonas putida (ATCC 21244),
Sarcina lutea (ATCC 9341),
Serratia liquefaciens (IFO 12979),
Serratia marcescens (IFO 3054),
Serratia marcescens (IFO 12648), and
Xanthobacter flavus (NCIMB 10071).

* * * * *